United States Patent
Williams, Jr. et al.

(10) Patent No.: US 8,540,683 B2
(45) Date of Patent: Sep. 24, 2013

(54) SYRINGE DEVICE AND INJECTOR SYSTEM INCLUDING A VENT FOR RELIEVING A VACUUM WITHIN A SYRINGE

(75) Inventors: Robert C. Williams, Jr., Fort Salonga, NY (US); Vito De Monte, North Babylon, NY (US)

(73) Assignee: ACIST Medical Systems, Inc., Eden Prairie, MN (US)

(*) Notice: Subject to any disclaimer, the term of this patent is extended or adjusted under 35 U.S.C. 154(b) by 850 days.

(21) Appl. No.: 11/539,805

(22) Filed: Oct. 9, 2006

(65) Prior Publication Data

US 2008/0171994 A1    Jul. 17, 2008

(51) Int. Cl.
*A61M 5/315*    (2006.01)

(52) U.S. Cl.
USPC .................. 604/230; 604/228; 604/218

(58) Field of Classification Search
USPC ............... 604/82, 89–91, 187, 218–223, 228, 604/230, 231, 235, 310, 311
See application file for complete search history.

(56) References Cited

U.S. PATENT DOCUMENTS

| | | |
|---|---|---|
| 4,869,720 A | 9/1989 | Chermack |
| 4,952,208 A | 8/1990 | Lix |
| 5,007,904 A | 4/1991 | Densmore |
| 5,085,638 A | 2/1992 | Farbstein |
| 5,181,912 A | 1/1993 | Hammett |
| 5,314,416 A | 5/1994 | Lewis |
| 5,383,858 A | 1/1995 | Reilly |
| 5,453,093 A | 9/1995 | Haining |
| 5,875,976 A | 3/1999 | Nelson |
| 5,947,929 A | 9/1999 | Trull |
| 6,752,789 B2 | 6/2004 | Duchon |
| 2002/0022807 A1 | 2/2002 | Duchon |
| 2004/0122369 A1 | 6/2004 | Schriver et al. |
| 2008/0183131 A1 | 7/2008 | Duchon |

FOREIGN PATENT DOCUMENTS

| | | |
|---|---|---|
| EP | 0 302 248 A1 | 2/1989 |
| EP | 0 599 649 A1 | 6/1994 |
| JP | 7-313598 | 12/1995 |
| WO | WO 92/01485 A1 | 2/1992 |
| WO | WO 96/30066 A1 | 10/1996 |
| WO | 9920330 | 4/1999 |
| WO | 9955401 | 11/1999 |
| WO | 0296487 | 12/2002 |
| WO | 2007062315 | 5/2007 |

OTHER PUBLICATIONS

The European Search Report for EP Appl. No. 07253965.3, completed Jan. 22, 2008.

(Continued)

*Primary Examiner* — Nicholas Lucchesi
*Assistant Examiner* — Nathan R Price
(74) *Attorney, Agent, or Firm* — Fredrikson & Byron, PA (57) ABSTRACT

A syringe device and injector system including a vent for relieving a vacuum within a syringe is provided. Embodiments provide a syringe device including a reservoir having a sidewall. The reservoir includes a dispensing distal end a proximal end. The syringe device also includes a piston in movable sealing engagement with the sidewall. Furthermore, the sidewall defines a vent extending from the proximal end of the reservoir. The vent is configured to interrupt the sealing engagement between the piston and the sidewall so as to allow a gas to enter the reservoir through the proximal aperture and past the piston member as the piston member is moved from the distal end to the proximal end of the tubular aperture.

48 Claims, 3 Drawing Sheets

(56) References Cited

OTHER PUBLICATIONS

The International Search Report and Written Opinion for International Application No. PCT/US2007/080815, completed Mar. 18, 2008, mailed Mar. 31, 2008.

International Search Report and Written Opinion, dated Feb. 25, 2010 for PCT Application No. PCT/US2009/064497, 11 pages.

International Search Report and Written Opinion, dated Mar. 1, 2010 for PCT Application No. PCT/US2009/064668, 11 pages.

ACIST CVi Contrast Delivery System User Manual, Nov. 2005, 91 pages. (P/N 900420-001 Rev. 04).

SYRINGE DEVICE AND INJECTOR SYSTEM INCLUDING A VENT FOR RELIEVING A VACUUM WITHIN A SYRINGE

FIELD OF THE INVENTION

The various embodiments of the present invention relate to the field of syringe devices, such as syringes adapted to be engaged with dispensing devices, which are used to dispense therapeutic and/or diagnostic agents to a subject. In one embodiment, the various embodiments of the present invention provide a syringe device capable of preventing potentially hazardous and/or damaging piston recoils in syringes having a piston member that may substantially evacuate the syringe when retracted.

BACKGROUND OF THE INVENTION

Conventional syringe devices, such as those adapted to be operably engaged with power injector devices, are designed to provide metered amounts of a particular therapeutic and/or diagnostic compound to a patient via needle, tube, catheter, and/or other conduit that may be operably engaged with a distal end of the syringe device. Conventional syringe devices provide a piston assembly that is movable between a distal end of the syringe device and a proximal end of the syringe device. Because the piston assembly is often engaged with an interior sidewall of the syringe reservoir in a substantially air-tight engagement (via one or more wiper seals, for example), the retraction of the piston assembly (towards the proximal end of the syringe assembly) may generate a substantial vacuum within the syringe assembly. The generation of a vacuum within a syringe assembly may be caused, for example, when a distal aperture (and/or a conduit downstream of such a distal aperture) defined in the syringe device, is partially or completely occluded (in some cases, by a closed check valve disposed downstream of the distal end of the syringe device).

For example, in some conventional contrast injection devices, a disposable syringe device may be operably engaged with the injection device. The injection device may be capable of automatically retracting the piston assembly to a "replace syringe" position near a proximal end of the syringe device such that the syringe device may be removable from the injection device to facilitate disposal and/or replacement of the syringe device. In some such devices, the movement of the piston assembly to the "replace syringe" position causes the injection device to automatically disengage from the piston assembly when the piston assembly reaches the proximal end of the syringe assembly. Thus, if a substantial vacuum has been created in the syringe device, the force of the vacuum may rapidly (and sometimes violently) draw the piston assembly towards the distal end of the syringe assembly when the injection device disengages the piston assembly. The resulting "piston slap" may, in turn, be violent enough to crack and/or shatter a portion of the syringe device.

Thus, there exists a need in the art for a "vented" or "self-venting" syringe assembly that is capable of relieving the vacuum generated in conventional syringe devices when, for example, a distal end of the syringe device is occluded during retraction of the piston assembly within the syringe. There further exists a need in the art for a disposable "vented" syringe that may be easily manufactured without adding substantial cost to the syringe device.

BRIEF SUMMARY OF THE INVENTION

The needs outlined above and others are met by the present invention which, in various embodiments, provides a syringe device that overcomes many of the technical problems discussed above. Specifically, in one embodiment, the syringe device comprises a reservoir having a reservoir sidewall defining an axis. The reservoir may comprise a dispensing distal end defining a dispensing aperture, and a proximal end defining a proximal aperture. The syringe device may further comprise a piston member movably disposed (e.g. slidably disposed) in the reservoir. Furthermore, the piston member can be movable between the distal end and the proximal end of the reservoir. In addition, the piston member may be in movable sealing engagement with the reservoir sidewall. The reservoir sidewall may define at least one longitudinally-extending vent extending from the proximal end of the reservoir. The vent may be configured to at least partially interrupt the sealing engagement between the piston member and the reservoir sidewall so as to allow a gas to enter the reservoir through the proximal aperture and past the piston member, thereby relieving any vacuum by equilibrating any internal syringe pressure relative to surrounding atmosphere, as the piston member is moved from the distal end to the proximal end.

According to various embodiments, the one or more vents may be defined in the sidewall of the reservoir such that a depth of the at least one vent decreases as the vent extends from the proximal end of the reservoir. Thus, according to such embodiments, the vent may be further configured to gradually and at least partially interrupt the sealing engagement between the piston member and the reservoir sidewall as the piston member is moved from the distal end to the proximal end of the reservoir. According to some embodiments, the piston member may be configured to be selectively movable to a maximum usable volume position disposed between the distal end and the proximal end of the reservoir. In such embodiments, the vent may extend from the proximal end of the reservoir to the maximum usable volume position (or just proximal thereto) so as to allow the gas to enter the reservoir through the proximal aperture and past the piston member, as the piston member is moved from the maximum usable volume position to the proximal end. Furthermore, according to various embodiments, the vent may define a cross-sectional shape that may include, but is not limited to: parabolic; polygonal; elliptical; circular; and combinations of such cross-sectional shapes.

In some embodiments, such as the injector system embodiments described herein, the reservoir may be adapted to be operably engaged with an injector device having a movable plunger head. According to some such embodiments, the piston member may comprise one or more (and preferably at least a pair of) gripping members configured to be positioned about a proximal edge of the piston member by the reservoir sidewall. Thus, in some embodiments, as the gripping members are positioned about the proximal edge of the piston member, the movable plunger head of the injector device is operably engaged between the piston member and the gripping members as the piston member is moved from the proximal end towards the distal end of the reservoir and back from the distal end to the proximal end. Furthermore, in order to facilitate the engagement of the reservoir with an injector device, the syringe device may, in some embodiments, further comprise a flange extending outward from the proximal end of the reservoir. The flange may be configured and/or sized to be received by a complementary channel (such as a radial groove, for example) defined in an injector device such that the syringe device may be selectively operably engaged with the injector device to form a complete injector system.

Thus, the various embodiments of the present invention provide many advantages that may include, but are not limited to: allowing for the relief of a vacuum that may be generated in a syringe; preventing potentially hazardous piston recoil within a syringe by allowing air to gradually vent into a syringe reservoir as a syringe piston is retracted prior to a release point near a proximal end of the syringe; providing a vented syringe that prevents piston recoil without incurring a substantial increase in unit cost or syringe complexity; and providing a vented syringe and compatible injector system that minimizes the chance of piston recoil, even in cases wherein a distal aperture of the syringe is occluded, for example.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Figure 1A:
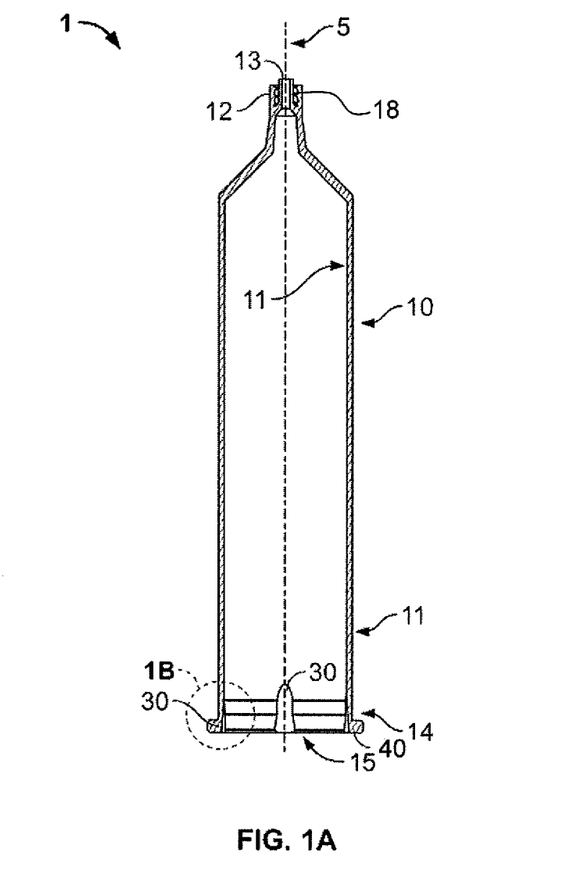
FIG. 1a is a non-limiting longitudinal cross-section of a reservoir, according to one embodiment of the present invention, wherein the reservoir sidewall defines at least one longitudinally-extending vent extending from the proximal end of the reservoir.
Figure 1B:
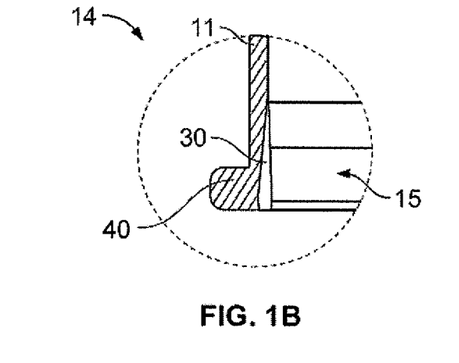
FIG. 1b is a non-limiting detailed longitudinal cross-section of a proximal end of a reservoir, according to one embodiment the present invention, wherein the reservoir sidewall defines at least one longitudinally-extending vent extending from the proximal end of the reservoir.
Figure 1C:
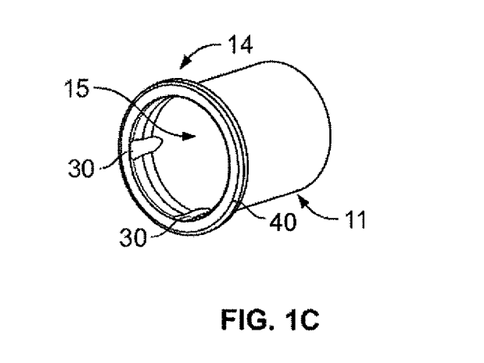
FIG. 1c is a non-limiting perspective view of a proximal end of a reservoir, according to one embodiment of the present invention, wherein the reservoir sidewall defines at least one longitudinally-extending vent extending from the proximal end of the reservoir.
Figure 2A:
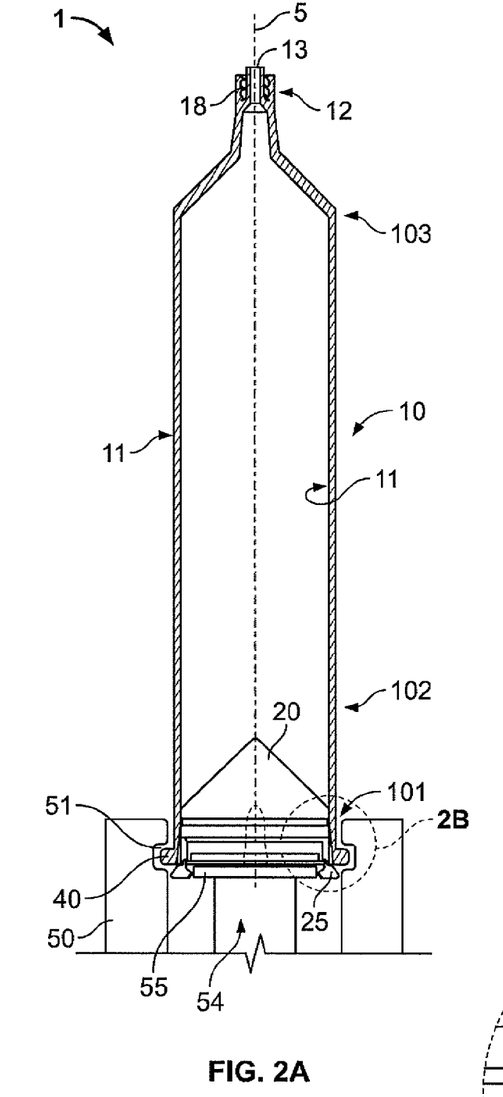
FIG. 2a is a non-limiting longitudinal cross-section of a reservoir and a piston member movably disposed therein, according to one embodiment of the present invention, wherein the reservoir sidewall defines at least one longitudinally-extending vent extending from the proximal end of the reservoir.
Figure 2B:
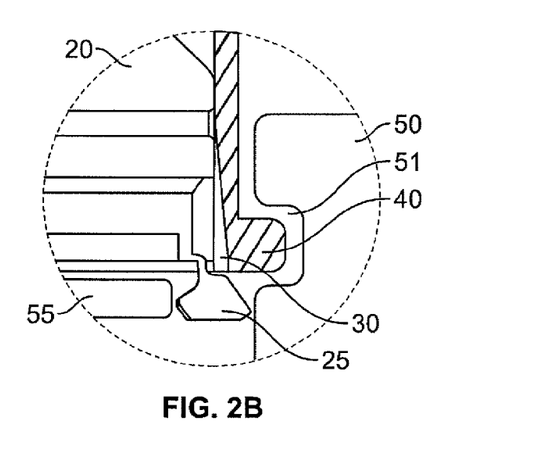
FIG. 2b is a non-limiting detailed longitudinal cross-section of a proximal end of a reservoir and a piston member movably disposed therein, according to one embodiment the present invention, wherein the reservoir sidewall defines at least one longitudinally-extending vent extending from the proximal end of the reservoir.

FIGS. 1a and 2b show a syringe device 1 according to one embodiment of the present invention wherein the syringe device 1 comprises a reservoir 10 having a reservoir sidewall 11 defining an axis 5, the reservoir 10 including a dispensing distal end 12 defining a dispensing aperture 13 and a proximal end 14 (see FIG. 1c, showing a detailed perspective view of the proximal end 14, according to one embodiment of the syringe device 1) defining a proximal aperture 15. According to various syringe device 1 embodiments of the present invention, the distal end 12 of the reservoir 10 may comprise a connector device 18 so as to enable the reservoir 10 (and/or the dispensing aperture 13 defined therein) to be operably engaged with a conduit for dispensing a therapeutic and/or diagnostic agent to a subject. The connector device 18 may comprise, for example, a threaded connector, barb connector, and/or luer lock assembly for operably engaging a conduit (that may include, but is not limited to: a tubing set, a catheter, a check valve, a manifold, a stop-cock and/or a needle assembly) with the dispensing distal end 12 of the reservoir 10. Furthermore, the connector device 18 may be configured to establish fluid communication between the dispensing aperture 13 and the conduit.

Furthermore, as described further herein, the proximal end 14 of the reservoir 10 may comprise a flange 40 extending radially outward from the proximal end 14. The flange 40 may be configured to be compatible with one or more channels 51 (such as one or more radial grooves, for example) defined in a complementary portion of an injector device 50 (such as a powered injector device, for example) to form a complete and/or a substantially complete injector system.

According to some embodiments, as shown generally in FIG. 1C, the reservoir 10 may define a substantially tubular shape. The reservoir 10 may also comprise a substantially polygonal cross-section (such as a square shape and/or an octagonal shape, for example). Furthermore, the reservoir may be formed from a variety of biocompatible and/or medical-grade materials suitable for disposable and/or reusable applications. For example, the reservoir 10 may comprise materials that may include but are not limited to: medical-grade polymer; glass, polymethyl methacrylate (PMMA); nylon; Pyrex; and/or combinations of such materials.

As shown in FIG. 2a, the syringe device 1 further comprises a piston member 20 movably disposed in the reservoir 10. For example, the piston member 20 may be slidably disposed in the reservoir 10. The piston member 20 is configured to be movable between the distal end 12 and the proximal end 14 (via interaction with a movable plunger head 55 of an injector device 50, for example, as described further herein). Furthermore, the piston member 20 is in movable sealing engagement with the reservoir sidewall 11 so as to prevent gasses from entering the reservoir 10 (via the proximal aperture 15, for example). The piston member 20 may, in some embodiments, be formed from a variety of biocompatible and/or medical-grade materials suitable for disposable and/or reusable applications. For example, the piston member 20 may comprise materials that may include but are not limited to: medical-grade polymer; rubber, silicone; and/or combinations of such materials. The piston member 20 may be formed in a variety of different cross-sectional shapes so as to conform to the overall internal shape of the reservoir 10 (so as to be capable of being in movable sealing engagement with the reservoir sidewall 11). For example, the piston member 20 may comprise a substantially polygonal cross-section (such as a square shape and/or an octagonal shape, for example), and/or a substantially circular and/or elliptical cross-section.

Figure 3:
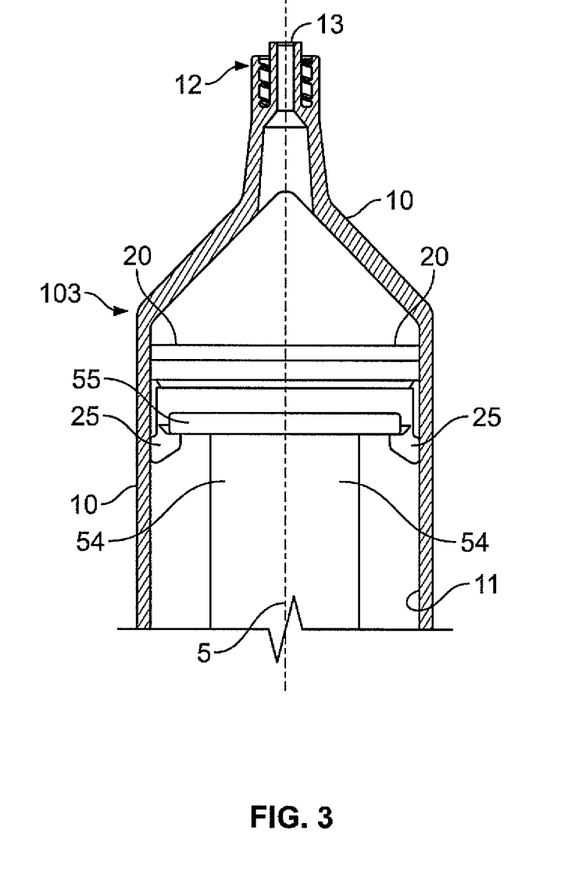
FIG. 3 is a non-limiting longitudinal cross-section of a distal end of a reservoir and a piston member movably disposed therein, according to one embodiment of the present invention, wherein the piston member is operably engaged with a movable plunger head of an injector device via a plurality of gripping members.

As shown generally in FIG. 1a, the reservoir sidewall 11 defines at least one longitudinally-extending vent 30 extending distally a length from the proximal end 14 of the reservoir 10. The vent 30 may be configured to at least partially interrupt the sealing engagement between the piston member 20 and the reservoir sidewall 11 so as to allow a gas to enter the reservoir ii through the proximal aperture 15 and past the piston member 20 as the piston member 20 is moved from the distal end 12 (see generally FIG. 3, showing the piston member 20 disposed near the distal end 12 of the reservoir 10 at a zero volume position 103) to the proximal end 14 (see generally FIG. 2a, showing the piston member 20 disposed near the proximal end 14 of the reservoir 10). According to various syringe device 1 embodiments of the present invention, the sidewall 11 of the reservoir 10 may define one or more vents 30 configured to at least partially interrupt the sealing engagement between the piston member 20 and the reservoir sidewall 11 so as to allow a gas to enter the reservoir ii through the proximal aperture 15 and past the piston member 20 as the piston member 20 is moved from the distal end 12 to the proximal end 14. For example, in some embodiments, 4 vents 30 may be defined in the sidewall 11 at 90 degree increments along an inner side of the reservoir sidewall 11 such that the sealing engagement between the piston member 20 and the reservoir sidewall 11 may be gradually and at least partially interrupted at four, substantially equally-spaced radial points along the inner sidewall 11 of the reservoir 10. Similarly, vents 30 may be geometrically different from one another in length and depth relative to the sidewall 11 such that sealing engagement between piston member 20 and the reservoir sidewall 11 may be selectively and/or partially interrupted.

According to some embodiments, the reservoir sidewall 11 may define at least one venting means (including, but not limited to the vent 30) for at least partially interrupting the sealing engagement between the piston member 20 and the reservoir sidewall 11. The venting means may thus allow a gas to enter the reservoir 10 through the proximal aperture 14 and past the piston member 20, as the piston member 20 is moved from the dispensing distal end 12 to the proximal end 14.

As shown generally in FIG. 1b, the vent 30 may be defined in the reservoir sidewall 11 such that a depth of the vent 30 decreases (e.g., along a majority of the length of the vent) as the vent 30 extends from the proximal end 14 of the reservoir 10. Thus, the vent 30 may be further configured to gradually and at least partially interrupt the sealing engagement between the piston member 20 and the reservoir sidewall 11 as the piston member 20 is moved from the distal end 12 (and/or a maximum usable volume position 102 (see FIG. 2a)) to the proximal end 14 of the reservoir 10. For example, as illustrated generally in FIG. 1c, the sidewall 11 may define four vents 30 having a generally parabolic cross-sectional shape. Such a vent 30 configuration may allow for the slight and/or gradual relief of a vacuum within the reservoir (by allowing gas to enter the reservoir past the piston member 20, for example, as shown generally in FIG. 2b) without allowing any fluid (such as residual contrast media, or other therapeutic and/or diagnostic compounds that may be contained within the reservoir 10) to escape via the vent 30. It should be understood that, in some embodiments, the vent 30 may extend to a position that is substantially proximal to (and/or lower than) the maximum usable volume position 102 (see FIG. 2a) such that even while the syringe device 1 is used to draw a therapeutic and/or diagnostic fluid into the reservoir 10 (up to the maximum usable volume position 102 (see FIG. 2a), for example), the vent 30 may not yet allow for air to enter the reservoir 10. Thus, the various syringe device 1 embodiments described herein may allow for the maintenance of a substantially sterile and/or air-tight reservoir 10 during the drawing and/or dispensing of therapeutic and/or diagnostic fluid and subsequently allow for air to vent into the reservoir (via the vent 30) so as to relieve a vacuum that may be formed as the piston member 20 is retracted (after a dispensing procedure, for example) from the distal end 12 (and/or a maximum usable volume position 102 (see FIG. 2a)) to the proximal end 14 of the reservoir 10.

In some embodiments, the vents 30 may define, in some embodiments, a plurality of corresponding radial points wherein the radial sealing force between a radially-outward surface of the piston member 20 and the radially-inward surface of the reservoir sidewall 11 is at least partially weakened such that the natural tendency of flowing air to relieve a vacuum may overcome the radial sealing force only at the radial points defined by the vents 30. However, the contact between the piston member 20 and the radially-inward surface of the reservoir sidewall 11 may still be sufficient (at the radial points established by the vents 30) to prevent the flow of liquid or other materials out of the reservoir 10 via the vents 30. In another embodiment, vents 30 can define a pre-sized gap between the radial sealing force element of the piston member 20 and the radially-inward surface of the reservoir sidewall 11 such that vacuum is automatically relieved, but any residual fluid in the syringe device 1 has sufficient surface tension to prevent inadvertent outward flow or nuisance leakage though the pre-sized gap. Furthermore, in some embodiments, a geometrical configuration of the at least one vent 30 may create at least a partial seal between the piston member 20 and the reservoir sidewall 11 such that a residual liquid is retained in the reservoir 10 while the partial seal succumbs to the pressure differential caused by a vacuum internal to the reservoir 10 so as to at least partially relieve the vacuum without allowing the residual liquid to flow outward from the reservoir 10 via the proximal aperture 15. For example, in some embodiments, the at lease one vent 30 may create an pathway between the piston member 20 and the reservoir sidewall 11 (see, for example, FIG. 2B) wherein the pathway is configured to allow relief of a vacuum internal to the reservoir 10 but small enough such that a surface tension of a residual liquid disposed in the reservoir 10 will prevent the residual liquid from flowing outward from the reservoir 10 via the proximal aperture 15.

Furthermore, while the vent 30 defined in the reservoir sidewall 11 (as pictured in FIG. 1c, for example), is shown with a generally parabolic cross-section, it should be understood that the vents 30 may include a variety of different cross-sectional shapes. For example, according to various embodiments of the present invention, the cross-sectional shape of the vent 30 may include, but is not limited to: parabolic; polygonal; elliptical; circular; and combinations of such cross-sectional shapes. Furthermore, the vents 30 may be formed in the reservoir sidewall 11 using a variety of methods. In some embodiments, the vents 30 may be substantially integrally formed in the reservoir sidewall 11. For example, in some syringe device 1 embodiments, the vents 30 may be molded into the sidewall 11 during an injection molding process for forming the reservoir 10. According to other embodiments, the vent 30 may be machined and/or otherwise mechanically defined in the reservoir sidewall 11 of a pre-assembled and/or pre-formed reservoir 10. In other embodiments, the vents 30 may be molded into an insert (such as a substantially annular insert, for example) that may be inserted into the proximal end 14 of the reservoir 10 and/or operably engaged therewith.

The vents 30 may thus allow for air to pass therethrough from an ambient environment into the reservoir 10 so as to relieve a substantial vacuum that may have been established therein as the piston member 20 is retracted from the distal end 12 of the reservoir 10 towards a proximal end 14 of the reservoir 10. As one skilled in the art will appreciate, such a vacuum may be established within the reservoir 10 when the dispensing aperture 13 of the reservoir 10 is substantially occluded (by a check valve (not shown)) or other device operably engaged in fluid communication with the dispensing aperture 13 of the reservoir 10. As described herein, the relief of the substantial vacuum established in the reservoir 10 may prevent the piston member 20 from being rapidly and/or violently drawn towards the distal end 12 of the reservoir 10 when the piston member 20 is released (either manually or automatically, for example) at some point near the proximal end 14 of the tubular member 12, as described further herein.

In some embodiments, as shown generally in FIG. 2a and FIG. 3, the piston member 20 may be further configured to be selectively movable to a maximum usable volume position 102 disposed substantially between the distal end 12 and the proximal end 14 of the reservoir 10. For example, the reservoir 10 (and the movable piston 20 disposed therein) may comprise a hypodermic syringe assembly as described in U.S. Pat. No. 4,869,720, which is hereby incorporated by reference herein in its entirety. As one skilled in the art will appreciate, such a syringe device 1, when provided in a "200 mL" size, may include a reservoir 10 including: (1) a zero-volume position 103 (wherein the piston member 20 is fully extended to the distal end 12 of the reservoir 10 (as shown generally in FIG. 3, for example)); (2) a maximum usable volume position 102 (such as a 200 mL volume position, wherein the piston member 20 is retracted to the full functional volume capacity of the reservoir 10); and (3) a "replace syringe" position 101 (wherein the piston member 20 is fully retracted). According to some such embodiments, the vent 30 may extend from the proximal end 14 (and/or the "replace syringe" position 101) of the reservoir 10 to (or just proximal to) the maximum usable volume position 102 so as to allow the gas to enter the reservoir 10 through the proximal aperture 15 and past the piston member 20 as the piston member 20 is moved from the maximum usable volume position 102 to the proximal end 14 (and/or the "replace syringe" position 101).

According to various embodiments, the syringe device 1 may comprise a reservoir 10 that is configured to be operably engaged with an injector device 50 including a movable plunger head 55 (mounted, for example, on a movable piston 54 movably engaged with the injector device 50 and/or a motor (not shown) thereof). According to some such embodiments, the syringe device 1 may be generally considered as a disposable and/or reusable component of an injector system that further comprises a reusable injector device 50. The injector device 50 may comprise, a number of different powered and/or electronically-controlled injector devices that may include, but are not limited to the Empower Injector System available from E-Z-EM, Inc. of Westbury, N.Y. For example, the reservoir 10 may comprise, in some embodiments, a flange 40 extending radially outward from the proximal end 14 of the reservoir 10. Furthermore, according to some injector system embodiments of the present invention, the injector device 50 may define a complementary channel 51 (such as a radial groove, for example) positioned and sized to receive the flange 40 of the reservoir 10 such that the syringe device 1 is adapted to be selectively operably engaged with the injector device 50 (as shown in FIGS. 2a and 2b, for example).

Furthermore, in some syringe device 1 embodiments (as shown in FIGS. 2a and 2b, for example), the piston member 20 may further comprise one or more (and preferably at least a pair of) gripping members 25. As shown in sequentially in FIG. 2b and FIG. 3, the gripping members 25 may include, but are not limited to: rotatable gripping members and flexible gripping members. Thus, the gripping members 25 may be configured to be rotated radially inward and/or flexed inward about a proximal edge of the piston member 20 by the reservoir sidewall 11 so as to operably engage the movable plunger head 55 of the injector device 50 between the piston member 20 and the rotatable and/or flexible gripping members 25 as the piston member 20 is moved from the proximal end 14 (and/or from the "replace syringe" position 101 (see FIGS. 2a and 2b)) towards the distal end 12 (see FIG. 3, showing the movable plunger head 55 operably engaged between the piston member 20 and the gripping members 25) and back to the proximal end 14. Thus, according to such embodiments, the gripping members 25 may be forced into engagement with the movable plunger head 55 of the injector device 50 only when the piston member 20 is disposed substantially distally from the "replace syringe" position 101.

Therefore, in such embodiments, if a substantial vacuum has been established in the reservoir 10 by the retraction of the piston member 20 (via the retraction of the movable plunger head 55, for example) from the zero-volume position 103 (as shown generally in FIG. 3, for example) to the maximum usable volume position 102, the continued retraction of the piston member 20 to the "replace syringe" position 101 may result in a violent piston member 20 recoil if the vacuum is not relieved (due to the disengagement of the rotatable and/or flexible gripping members 25 from the movable plunger head 55 (see FIG. 2a, for example)). Thus, according to such embodiments, the vent 30 defined in the sidewall 11 of the tubular member 10 allows for the gradual relief of the vacuum that may be established in the reservoir 10 (especially if a dispensing aperture 13 thereof is occluded) as the piston member 20 is retracted from the maximum usable volume position 102 to the "replace syringe" position 101.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A syringe device comprising:
 a reservoir having a reservoir sidewall defining an axis, the reservoir comprising a dispensing distal end defining a dispensing aperture and a proximal end defining a proximal aperture; and
 a piston member movably disposed in the reservoir, the piston member being configured to be movable between the distal end and the proximal end, the piston member being in movable sealing engagement with the reservoir sidewall;
 wherein the reservoir sidewall defines at least one longitudinally-extending vent extending distally a length from the proximal end of the reservoir, a depth of the at least one vent continually decreasing at an angle relative to the axis along a majority of the length of the vent as the at least one vent extends from the proximal end of the reservoir, the angle being constant along a majority of the vent, such that the at least one vent is configured to gradually and at least partially interrupt the sealing engagement between the piston member and the reservoir sidewall so as to allow a gas to enter the reservoir through the proximal aperture and past the piston member, as the piston member is moved from the distal end to the proximal end.

2. A syringe device according to claim 1, wherein the reservoir defines a substantially tubular shape.

3. A syringe device according to claim 1, wherein the reservoir is formed from a medical-grade polymer.

4. A syringe device according to claim 1, wherein the reservoir is formed from a glass material.

5. A syringe device according to claim 1, wherein the piston member is formed of a medical-grade polymer.

6. A syringe device according to claim 1, wherein the piston member is formed of a rubber material.

7. A syringe device according to claim 1, further comprising a connector device operably engaged with the dispensing distal end of the reservoir for operably engaging at least one conduit with the reservoir, the connector device configured to be in fluid communication between the dispensing aperture and the at least one conduit.

8. A syringe device according to claim 1, wherein the at least one vent is substantially integrally formed in the reservoir sidewall.

9. A syringe device according to claim 1, wherein a geometrical configuration of the at least one vent creates at least a partial seal between the piston member and the reservoir sidewall such that a residual liquid is retained in the reservoir while the partial seal succumbs to the pressure differential caused by a vacuum internal to the reservoir so as to at least partially relieve the vacuum without allowing the residual liquid to flow outward from the reservoir via the proximal aperture.

10. A syringe device according to claim 1, wherein the at lease one vent creates a pathway between the piston member and the reservoir sidewall, the pathway being configured to allow relief of a vacuum internal to the reservoir and such that a surface tension of a residual liquid disposed in the reservoir will prevent the residual liquid from flowing outward from the reservoir via the proximal aperture.

11. A syringe device according to claim 1, wherein the piston member is further configured to be selectively movable to a maximum usable volume position disposed substantially between the distal end and the proximal end of the reservoir, and wherein the at least one vent extends from the proximal end of the reservoir to the maximum usable volume position so as to allow the gas to enter the reservoir through the proximal aperture and past the piston member, as the piston member is moved from the maximum usable volume position to the proximal end.

12. A syringe device according to claim 1, wherein the syringe device is configured to be selectively operably engaged and disengaged with the injector device, wherein the reservoir is adapted to be operably engaged with an injector device including a movable plunger head and wherein the piston member further comprises one or more gripping members the gripping members configured to be forced by the reservoir sidewall to operably engage the movable plunger head in response to distal movement of the movable plunger head into the reservoir at the proximal end, the gripping members further configured to operably disengage the movable plunger head in response to proximal movement of the movable plunger head out of the reservoir at the proximal end.

13. A syringe device according to claim 12, wherein the gripping members comprise rotatable gripping members configured to be rotated radially-inward about the proximal edge of the piston member by the reservoir sidewall as the piston member is moved between the proximal end and the distal end so as to operably engage the movable plunger head and configured to be rotated radially-outward about the proximal edge of the piston member so as to operably disengage the movable plunger head at the proximal end.

14. A syringe device according to claim 12, wherein the gripping members comprise substantially flexible gripping members configured to be flexed inward about the proximal edge of the piston member by the reservoir sidewall as the piston member is moved between the proximal end and the distal end so as to operably engage the movable plunger head and configured to be flexed radially-outward about the proximal edge of the piston member so as to operably disengage the movable plunger head at the proximal end.

15. A syringe device according to claim 1, wherein a shape of the at least one vent is polygonal.

16. A syringe device according to claim 1, wherein a shape of the at least one vent is elliptical.

17. A syringe device according to claim 1, wherein a shape of the at least one vent is circular.

18. A syringe device according to claim 1, further comprising a flange extending outward from the proximal end of the reservoir, the flange being adapted to be received by a complementary channel defined in an injector device such that the syringe device is adapted to be selectively operably engaged with the injector device.

19. A syringe device according to claim 18, wherein the flange extends radially outward from the proximal end of the reservoir.

20. A syringe device according to claim 18, wherein the complementary channel is defined in the injector device as a radial groove.

21. A syringe device according to claim 1, wherein the at least one vent comprises a generally parabolic cross-sectional shape.

22. A syringe device according to claim 1, wherein the reservoir sidewall has inner and outer surfaces and a thickness extending therebetween, and wherein the longitudinally-extending vent is defined within the thickness of the inner surface such that the sidewall is thinner along at least a portion of the longitudinally-extending vent.

23. A syringe device according to claim 22, wherein the reservoir has an outer diameter, and wherein the outer diameter is constant along its length and at least partially along the outer surface opposite the longitudinally-extending vent.

24. A syringe device according to claim 1, wherein the depth of the at least one vent gradually decreases along a substantial length of the vent between the proximal end of the reservoir and a distal end of the vent.

25. An injector system comprising:
an injector device including a movable plunger head; and
a syringe device configured to be capable of operably engaging the injector device, the syringe device comprising:
a reservoir having a reservoir sidewall defining an axis, the reservoir including a dispensing distal end defining a dispensing aperture and a proximal end defining a proximal aperture; and
a piston member movably disposed in the reservoir, the piston member being configured to be operably engaged with the movable plunger head so as to be movable between the distal end and the proximal end, the piston member being in movable sealing engagement with the reservoir sidewall;
wherein the reservoir sidewall defines at least one longitudinally-extending vent extending distally a length from the proximal end of the reservoir, a depth of the at least one vent continually gradually decreasing at an angle relative to the axis along a majority of the length of the vent as the at least one vent extends from the proximal end of the reservoir, the angle being constant along a majority of the vent, such that the at least one vent is configured to gradually and at least partially interrupt the sealing engagement between the piston member and the reservoir sidewall so as to allow a gas to enter the reservoir through the proximal aperture and past the piston member, as the piston member is moved from the distal end to the proximal end.

26. An injector system according to claim 25, wherein the reservoir defines a substantially tubular shape.

27. An injector system according to claim 25, wherein the reservoir is formed from a medical-grade polymer.

28. An injector system according to claim 25, wherein the reservoir is formed from a glass material.

29. An injector system according to claim 25, wherein the piston member is formed of a medical-grade polymer.

30. An injector system according to claim 25, wherein the piston member is formed of a rubber material.

31. An injector system according to claim 25, further comprising a connector device operably engaged with the dispensing distal end of the reservoir for operably engaging at least one conduit with the reservoir, the connector device configured to be in fluid communication between the dispensing aperture and the at least one conduit.

32. An injector system according to claim 25, wherein the at least one vent is substantially integrally formed in the reservoir sidewall.

33. An injector system according to claim 25, wherein the piston member is further configured to be selectively movable to a maximum usable volume position disposed substantially between the distal end and the proximal end of the reservoir, and wherein the at least one vent extends from the proximal end of the reservoir to the maximum usable volume position so as to allow the gas to enter the reservoir through the proximal aperture and past the piston member, as the piston member is moved from the maximum usable volume position to the proximal end.

34. An injector system according to claim 25, wherein the syringe device is configured to be selectively operably engaged and disengaged with the injector device, wherein the piston member further comprises one or more gripping members, the gripping members being configured to be forced by the reservoir sidewall to operably engage the movable plunger head in response to distal movement of the movable plunger head into the reservoir at the proximal end, the gripping members further configured to operably disengage the movable plunger head in response to proximal movement of the movable plunger head out of the reservoir at the proximal end.

35. An injector system according to claim 34, wherein the gripping members comprise rotatable gripping members configured to be rotated radially-inward about the proximal edge of the piston member by the reservoir sidewall as the piston member is moved between the proximal end and the distal end so as to operably engage the movable plunger head and configured to be rotated radially-outward about the proximal edge of the piston member so as to operably disengage the movable plunger head at the proximal end.

36. An injector system according to claim 34, wherein the gripping members comprise substantially flexible gripping members configured to be flexed inward about the proximal edge of the piston member by the reservoir sidewall as the piston member is moved between the proximal end and the distal end so as to operably engage the movable plunger head and configured to be flexed radially-outward about the proximal edge of the piston member so as to operably disengage the movable plunger head at the proximal end.

37. An injector system according to claim 25, wherein the shape of the at least one vent is polygonal.

38. An injector system according to claim 25, wherein the shape of the at least one vent is elliptical.

39. An injector system according to claim 25, wherein the shape of the at least one vent is circular.

40. An injector system according to claim 25, wherein the syringe device further comprises a flange extending outward from the proximal end of the reservoir, and wherein the injector device defines a channel therein for receiving the flange such that the syringe device is configured to be selectively operably engaged with the injector device.

41. An injector system according to claim 40, wherein the flange extends radially outward from the proximal end of the reservoir.

42. An injector device according to claim 40, wherein the complementary channel is defined in the injector device as a radial groove.

43. An injector system according to claim 25, wherein the at least one vent comprises a generally parabolic cross-sectional shape.

44. An injector system according to claim 25, wherein the reservoir sidewall has inner and outer surfaces and a thickness extending therebetween, and wherein the longitudinally-extending vent is defined within the thickness of the inner surface such that the sidewall is thinner along at least a portion of the longitudinally-extending vent.

45. An injector system according to claim 44, wherein the reservoir has an outer diameter, and wherein the outer diameter is constant along its length and at least partially along the outer surface opposite the longitudinally-extending vent.

46. An injector system according to claim 25, wherein the depth of the at least one vent gradually decreases along a substantial length of the vent between the proximal end of the reservoir and a distal end of the vent.

47. A syringe device comprising:
a reservoir having a reservoir sidewall defining an axis, the reservoir comprising a dispensing distal end defining a dispensing aperture and a proximal end defining a proximal aperture; and
a piston member movably disposed in the reservoir, the piston member being configured to be movable between the distal end and the proximal end, the piston member being in movable sealing engagement with the reservoir sidewall;
wherein the reservoir sidewall defines at least one venting means for at least partially interrupting the sealing engagement between the piston member and the reservoir sidewall so as to allow a gas to enter the reservoir through the proximal aperture and past the piston member, as the piston member is moved from the distal end to the proximal end,
wherein the reservoir is adapted to be selectively operably engaged and disengaged with an injector device including a movable plunger head and wherein the piston member further comprises one or more gripping members, the gripping members configured to be forced by the reservoir sidewall to operably engage the movable plunger head in response to distal movement of the movable plunger head into the reservoir at the proximal end, the gripping members further configured to operably disengage the movable plunger head in response to proximal movement of the movable plunger head out of the reservoir at the proximal end.

48. A syringe device comprising:
a reservoir having a reservoir sidewall defining an axis, the reservoir comprising a dispensing distal end defining a dispensing aperture and a proximal end defining a proximal aperture, the reservoir further comprising a flange extending radially outward from the proximal end; and a piston member movably disposed in the reservoir, the piston member being configured to be movable between the distal end and the proximal end, the piston member being in movable sealing engagement with the reservoir sidewall, wherein the reservoir sidewall defines at least one longitudinally-extending vent extending distally a length from the proximal end of the reservoir, a depth of the at least one vent continually decreasing at an angle relative to the axis along a majority of the length of the vent as the at least one vent extends from the proximal end of the reservoir, the angle being constant along a majority of the vent, such that the at least one vent is configured to gradually and at least partially interrupt the sealing engagement between the piston member and the reservoir sidewall so as to allow a gas to enter the reservoir through the proximal aperture and past the piston member, as the piston member is moved from the distal end to the proximal end, and wherein the reservoir sidewall has inner and outer surfaces and a thickness extending therebetween, and wherein the longitudinally-extending vent is defined within the thickness of the inner surface such that the sidewall is thinner along at least a portion of the longitudinally-extending vent distally of the flange.

\* \* \* \* \*